United States Patent [19]

Zeffren et al.

[11] 3,957,424

[45] May 18, 1976

[54] ENZYME-ACTIVATED OXIDATIVE PROCESS FOR COLORING HAIR

[75] Inventors: Eugene Zeffren, Montgomery; John Francis Sullivan, Cincinnati, both of Ohio

[73] Assignee: The Procter & Gamble Company, Cincinnati, Ohio

[22] Filed: Sept. 13, 1974

[21] Appl. No.: 505,698

Related U.S. Application Data

[63] Continuation-in-part of Ser. No. 193,182, Oct. 27, 1971, abandoned, which is a continuation-in-part of Ser. No. 88,143, Nov. 9, 1970, abandoned.

[52] U.S. Cl.................................... 8/10.2; 8/10; 8/10.1; 8/11; 8/32
[51] Int. Cl.².......................................... A61K 7/13
[58] Field of Search.................... 8/10.2, 11, 32

[56] References Cited

UNITED STATES PATENTS

| | | | |
|---|---|---|---|
| 2,539,202 | 1/1951 | Peck | 8/10.2 |
| 3,200,040 | 8/1965 | Lange | 8/10.2 |
| 3,210,252 | 10/1965 | Blanke et al. | 8/10.2 |
| 3,251,742 | 5/1966 | Soloway | 8/10.2 |

*Primary Examiner*—Norman A. Drezin
*Assistant Examiner*—Vera C. Clarke
*Attorney, Agent, or Firm*—Charles R. Wilson; Richard C. Witte; Thomas H. O'Flaherty

[57] ABSTRACT

An enzyme-based oxidative process for coloring hair wherein the hair is exposed to a solution having a pH of about 4 to about 10 and containing hydrogen peroxide, soybean peroxidase enzyme and one or more oxidation dye precursors.

15 Claims, No Drawings

ENZYME-ACTIVATED OXIDATIVE PROCESS FOR COLORING HAIR

CROSS REFERENCE TO RELATED APPLICATION

This application is a continuation-in-part of copending application, Ser. No. 193,182, filed Oct. 27, 1971, now abandoned, which is in turn a continuation-in-part of application, Ser. No. 88,143, filed Nov. 9, 1970, now abandoned.

BACKGROUND OF THE INVENTION

This invention relates to an enzyme activated process for coloring hair.

Pre-formed dyes for coloring hair have not gained wide acceptance due to their general failure to impart colors to hair which are sufficiently imitative of natural hair colors. Products which contain reactants such as $H_2O_2$ and an oxidation dye precursor (i.e., a precursor which forms dyes in situ on the hair through an oxidative process) do produce colors which are closely imitative of natural hair color and have obtained reasonable commercial success. These latter products, however, because of the severe oxidizing conditions required (i.e., performing the oxidation at $H_2O_2$ concentration of 3% or more and a pH of 8.5 or higher for time periods in excess of 20 minutes) and the high concentrations of oxidation dye precursors needed to produce the desired coloration can cause skin irritation and sensitizatin as well as hair damage to some users. Further, the ammonium hydroxide which is generally used to maintain the high pH in these products has an odor which is offensive to most users.

U.S. Pat. No. 3,251,742, issued May 17, 1966, teaches an enzyme based oxidative process for dyeing hair at substantially neutral pH, wherein oxygen from the atmosphere is the oxidizing agent. The enzyme is an oxidase (e.g., tyrosinase or laccase) and the dye precursor is a combination of an aromatic polyhydric compound and an aromatic amine. Surprisingly, it has been found, according to the process of the present invention, that an oxidative coloring process based on hydrogen peroxide and soybean peroxidase enzyme can be carried out under mild oxidizing conditions and does not require a dual oxidation dye precursor system comprising an aromatic polyhydric compound and an aromatic amine. Either type of compound can be used alone as the oxidation dye precursor in the present invention. This provides more flexibility in selection of the oxidation dye precursors and thus more freedom in the choice of colors to be produced.

DESCRIPTION OF THE INVENTION

The object of the invention herein is to provide an improved mild oxidative process for coloring hair.

This and other objects, which will become apparent, are achieved by the invention herein which is an enzyme-activated oxidative process for coloring hair wherein hydrogen peroxide is used as the oxidizing agent. The enzyme used in the process herein is soybean peroxidase and the process comprises contacting the hair with a solution comprising soybean peroxidase enzyme, hydrogen peroxide and one or more oxidation dye precursors (as hereinafter defined), said solution having a pH of from about 4.0 to about 10.0, preferably from about 5.5 to about 8.0.

Soybean peroxidase is a member of the peroxidase enzyme family classified in Class 1.11 [i.e., Class 1, Subclass 11 of the Recommendation (1964) of the International Union of Biochemistry on the Nomenclature and Classification of Enzymes], which catalyze the oxidation of various materials (including the oxidation dye precursors herein) by hydrogen peroxide. Soybean peroxides is, as its name implies, derived by known methods from the soybean hull.

The soybean peroxidase enzyme can be used in its pure crystalline form, which is obtained by isolating the enzyme from other materials present during preparation, or it can be used in a diluted form where the enzyme is present in a composition along with these materials and/or added inert diluents.

Commercially available enzyme preparations normally contain the enzyme in combination with inert diluent and carrier materials such as carbohydrates, agglutinating proteins, inorganic salts such as sodium sulfate, calcium sulfate, and the like. In such preparations the enzyme constitutes a minor component and comprises from about 1% to about 50% by weight of the preparation. The remaining 50% to 99% is comprised of the hereinbefore described diluents and carriers. The commercially available enzyme-containing preparations are preferred as sources of enzyme herein as they are more readily available than the pure crystalline enzyme and provide known, pre-determined and desirable levels of enzyme activity.

In the coloring process herein, soybean peroxidase enzyme is used at concentrations of from about 0.01 ppm to about 500 ppm, and preferably from about 0.05 ppm to about 100 ppm in the coloring solution. These levels are based on weight of pure enzyme. If a commercial enzyme preparation is used wherein the enzyme is combined with diluents and carriers, as hereinbefore described, the concentration of the enzyme preparation will have to be proportionately higher in order to achieve the required concentration of pure enzyme. The amount of pure enzyme present in such compositions can be readily determined by known assay methods.

The oxidation dye precursors which are used in the compositions and processes herein include aromatic diamines, various substituted phenols, amino phenols and derivatives of these aromatic compounds (e.g., N-substituted derivatives of the amines and ethers of the phenols). The oxidation dye precursors useful herein can be classified as "primary oxidation dye precursors" and "secondary oxidation dye precursors", as detailed hereinafter. In general terms, oxidation hair dye precursors include those monomeric aromatic compounds which, on oxidation, form aligomers or polymers having extended conjugated systems of electrons in their molecular structure. Because of the new electronic structure, the resultant oligomers and polymers exhibit a shift in their electronic spectra to the visible range and appear colored. For example, oxidation dye precursors capable of forming colored polymers include materials such as various aromatic amines having a single functional group and which, on oxidation, form a series of conjugated imines and quinonoid dimers, trimers, etc. ranging in color from green to black. Compounds, such as p-phenylenediamine, which have two functional groups are capable of oxidative polymerization to yield higher molecular weight colored materials having extended conjugated electron systems, i.e., the so-called "Bandrowski's Base" type of dye compound. Color modifiers, such as those detailed hereinafter as "secondary oxidation dye precursors", can optionally be used in conjunction with the primary oxidation dye precursors herein and are thought to interpose themselves in the colored polymers during their formation and to cause shifts in the electronic spectra thereof, thereby resulting in changes in color and/or color intensity. It is to be understood that the peroxidase enzymes disclosed herein are suitable for use (in conjunction with a peroxide source, e.g., $H_2O_2$, as detailed herein) with all manner of primary and secondary oxidation dye precursors. A representative list of oxidation dye precursors suitable for use herein is found in Sagarin, "Cosmetic Science and Technology", Interscience, pages 504 and 508, and the dye precursors detailed below are only by way of example and are not intended to limit the compositions and processes herein. Additional oxidation dye precursors useful herein are described in French Application No. 1,318,072 and Fr. Addition 90,633, Jan. 19, 1968, to Schwarzkopf; British Pat. No. 1,127,080, Sept. 11, 1968, to Kalopissis and Bugaut; and Netherlands Application No. 6,609,833, Feb. 6, 1967, to Therachemie Chemisch Therapeutische G.m.b.H., incorporated herein by reference. Pyridine, quinoline, isoquinoline oxidation dye precursors such as those disclosed by Berqwein, *Reichst., Aromen, Koerperpflegem.* 17 (14) 136–8 (1967), are also suitable herein.

The oxidation dye precursors which are used in the process of the present invention can be divided into two classes, primary and secondary. The primary oxidation dye precursors are essential to the practice of the invention and include those aromatic diamines, polyhydric phenols, amino phenols and derivatives of these aromatic compounds (e.g., N-substituted derivatives of the amines, and ethers of the phenols) which produce color formation in the following test, which is performed at room temperature (about 18° to 28°C.).

PRIMARY DYE PRECURSOR TEST 10 ml. of aqueous buffer (pH 5 to 8) containing 0.01% to 1.0% (by weight) $H_2O_2$ is mixed with 0.1 to 1.0 ml. of a 1% (by weight) aqueous or alcoholic solution of the precursor. To this mixture is added an amount of horseradish peroxidase such that the final mixture contains 0.01 to 100 ppm peroxidase (based on weight of pure enzyme). The mixture is left standing to allow color formation. A suitable primary oxidation dye precursor will give color formation within 5 minutes. Some oxidation dye precursors, because of their self-color, impart a pale color to the solution before addition of enzyme. Color formation, in this test, refers to a visually perceptible color change which occurs after the addition of enzyme.

The aromatic diamines, polyhydric phenols, amino phenols, and derivatives thereof, described above as primary oxidation dye precursors, can also have additional substituents on the aromatic ring, e.g., halogen, aldehyde, carboxylic acid, and substituted and unsubstituted hydrocarbon groups, as well as additional substituents on the amino nitrogen, and on the phenolic oxygen, e.g., substituted and unsubstituted alkyl and aryl groups.

Examples of aromatic diamines and derivatives thereof, amino phenols and derivatives thereof and polyhydric phenols and derivatives thereof, respectively, are compounds having the general formulas (A), (B) and (C) below:

(A) 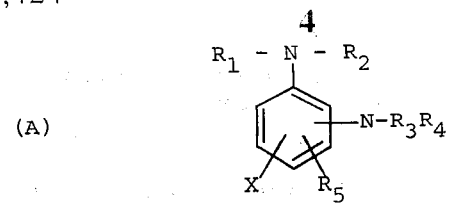

wherein X is hydrogen, halogen, (e.g., fluorine, chlorine, bromine or iodine), amino, hydroxyl,

(wherein M is hydrogen or an alkali or alkaline earth metal, ammonium, or substituted ammonium wherein one or more hydrogens on the ammonium ion is replaced with a 1 to 3 carbon atom alkyl or hydroxy alkyl radical), wherein $R_1$, $R_2$, $R_3$, and $R_4$ are the same or different from each other and are selected from the group consisting of hydrogen, $C_1$ to $C_4$ alkyl or alkenyl and $C_6$ to $C_9$ aryl, alkaryl or aralkyl, and $R_5$ is hydrogen, $C_1$ to $C_4$ alkyl or alkenyl (including substituted alkyl or alkenyl wherein the substituents are selected from those designated as X, above) or $C_6$ to $C_9$ aryl, alkaryl or aralkyl (including substituted alkyl, alkaryl or aralkyl groups wherein the substituents are selected from those defined as X, above). Specific examples of formula (A) compounds are:

o-phenylenediamine
m-phenylenediamine
p-phenylenediamine
2-chloro-p-phenylenediamine
2-iodo-p-phenylenediamine
1,3,5-triaminobenzene
2-hydroxy-p-phenylenediamine
2,4-diaminobenzoic acid
sodium 2,4-diaminobenzoate
calcium di-2,4-diaminobenzoate
ammonium 2,4-diaminobenzoate
trimethylammonium 2,4-diamineobenzoate
tri-(2-hydroxyethyl)ammonium 2,4-diaminobenzoate
2,4-diaminobenzaldehyde
2,4-diaminobenzenesulfonic acid
potassium 2,4-diaminobenzenesulfonate
N,N-diisopropyl-p-phenylenediamine
N,N-dimethyl-p-phenylenediamine
N-methyl-N'-(2-propenyl)-p-phenylenediamine
N-phenyl-p-phenylenediamine
N-phenyl-N-benzyl-p-phenylenediamine
N-ethyl-N'-(3-ethylphenyl)-p-phenylenediamine
2,4-toluenediamine
2-ethyl-p-phenylenediamine
2-(2-bromoethyl)-p-phenylenediamine
2-phenyl-p-phenylenediamine
4-(2,5-diaminophenyl)benzaldehyde
2-benzyl-p-phenylenediamine
2-(4-nitrobenzyl)-p-phenylenediamine
2-(4-methylphenyl)-p-phenylenediamine
2-(2,5-diaminophenyl)-5-methylbenzoic acid (B) 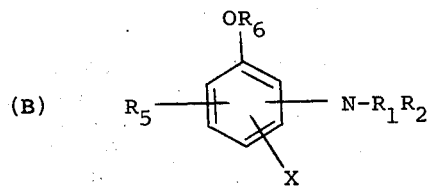

where X is the same as in formula (A), $R_1$ and $R_2$ can be the same or different from each other and are the same as in formula (A), $R_5$ is the same as in formula (A) and $R_6$ is hydrogen or $C_1$ to $C_4$ alkyl or alkenyl (including substituted alkyl or alkenyl wherein the substituents are selected from those defined as X in formula (A), above). Specific examples of formula (B) compounds are:

o-aminophenol
m-aminophenol
p-aminophenol
2-chloro-p-aminophenol
2-iodo-p-aminophenol
2-nitro-p-aminophenol
3,4-dihydroxyaniline
3,4-diaminophenol
2-hydroxy-4-aminobenzoic acid
2-hydroxy-4-aminobenzaldehyde
3-amino-4-hydroxybenzenesulfonic acid
N,N-diisopropyl-p-aminophenol
N-methyl-N-(1-propenyl)-p-aminophenol
N-phenyl-N-benzyl-p-aminophenol
N-methyl-N-(3-ethylphenyl)-p-aminophenol
(2-hydroxy-5-aminophenyl)acetaldehyde
2-methyl-p-aminophenol
(2-hydroxy-5-aminophenyl)acetic acid
3-(2-hydroxy-5-aminophenyl)-1-propene
3-(2-hydroxy-5-aminophenyl)-2-chloro-1-propene
2-phenyl-p-aminophenol
2-(4-nitrophenyl)-p-aminophenol
2-benzyl-p-aminophenol
2-(4-chlorobenzyl)-p-aminophenol
2-(4-methylphenyl)-p-aminophenol
2-(2-amino-4-methylphenyl)-p-aminophenol
p-methoxyaniline
2-bromoethyl-4-aminophenyl ether
2-nitroethyl-4-aminophenyl ether
2-aminoethyl-4-aminophenyl ether
2-hydroxyethyl-4-aminophenyl ether
(4-aminophenoxy)acetaldehyde
(4-aminophenoxy)acetic acid
(4-aminophenoxy)methanesulfonic acid
1-propenyl-4-aminophenyl ether
(2-chloro)-1-propenyl-4-aminophenyl ether
(2-amino)-1-propenyl-4-aminophenyl ether
(2-hydroxy)-1-propenyl-4-aminophenyl ether (C) 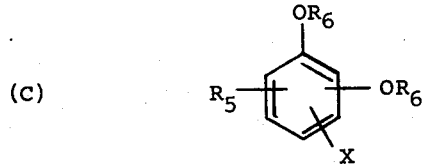

where X, $R_5$ and $R_6$ are as defined above in formula (B). Specific examples of formula (C) compounds are:
o-hydroxyphenol
m-hydroxyphenol
p-hydroxyphenol
4-methoxyphenol
2-methoxyphenol
4-(2-chloroethoxy)phenol
4-(2-propenoxy)phenol
4-(3-chloro-2-propenoxy)phenol
2-chloro-4-hydroxyphenol 2-amino-4-hydroxyphenol
1,3,5-trihydroxybenzene
2,4-dihydroxybenzaldehyde
3,4-dihydroxybenzaldehyde
3,4-dihydroxybenzoic acid
2,4-dihydroxybenzenesulfonic acid
3-ethyl-4-hydroxyphenol
3-(2-nitroethyl)-4-hydroxyphenol
3-(2-propenyl)-1-hydroxyphenol
3-(3-chloro-2-propenyl)-4-hydroxyphenol
2-phenyl-4-hydroxyphenol
2-(4-chlorophenyl)-4-hydroxyphenol
2-benzyl-4-hydroxyphenol
2-(2-methylphenyl)-4-hydroxyphenol
2-(2-methyl-4-chlorophenyl)-4-hydroxyphenol
3-methoxy-4-hydroxy-benzaldehyde
2-methoxy-4-(1-propenyl)phenol
4-hydroxy-3-methoxycinnamic acid
2,5-dimethoxyaniline The secondary oxidation dye precursors are optionally employed in the process of this invention and include those aromatic amines and phenols and derivatives thereof which do not produce color formation in the above test but which modify the color, shade or intensity of color developed by primary dye precursors. Various aromatic amines and phenolic compounds, and derivatives thereof, including aromatic diamines and polyhydric phenols of the types described by formulas (A), (B) and (C) above, but which are found by the above test not to be suitable primary oxidation dye precursors, are suitable as secondary dye precursors if they are capable of modifying the color, shade or intensity of color produced by primary oxidation dye precursors in the following test, which is conducted at room temperature (about 18° to 28°C.).

SECONDARY DYE PRECURSOR TEST

Two solutions are prepared as follows:
10 ml of aqueous buffer (pH 5 to 8) containing 0.01% to 1.0% (by weight) $H_2O_2$ is mixed with 0.1 to 1.0 ml of a 1% (by weight) aqueous or alcoholic solution of primary precursor. 0.1 to 1.0 ml. of a 1.0% (by weight) aqueous or alcoholic solution of the potential secondary dye precursor is added to one of the solutions and then an amount of horseradish peroxidase is added to each solution such that the final enzyme concentration is 0.01 to 100 ppm (based on weight of pure enzyme). The solutions are left to stand for 5 minutes to permit development of color. A suitable secondary oxidation dye precursor will cause the second solution to differ from the first solution in color, shade or intensity of color.

The aromatic amines and phenols and derivatives described above as secondary oxidation dye precursors can also have additional substituents on the aromatic ring, e.g., halogen, aldehyde, carboxylic acid, nitro, sulfonyl and substituted and unsubstituted hydrocarbon groups, as well as additional substituents on the amino nitrogen, or phenolic oxygen, e.g., substituted and unsubstituted alkyl and aryl groups.

Examples of aromatic amines, phenols and derivatives thereof are compounds of the general formulas (D) and (E) below:

(D) 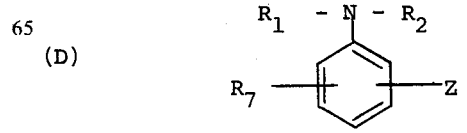

wherein Z is hydrogen, $C_1$ to $C_3$ alkyl, halogen (e.g., fluorine, chlorine, bromine or iodine), nitro,

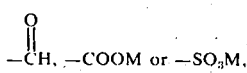

(where M is hydrogen or an alkali or alkaline earch metal, ammonium or substituted ammonium wherein one or more hydrogens on the ammonium ion is replaced with a 1 to 3 carbon atom alkyl or hydroxy alkyl radical), wherein $R_1$ and $R_2$ are the same or different and are each selected from the group consisting of hydrogen, $C_1$ to $C_4$ alkyl or alkenyl and $C_6$ to $C_9$ aryl, alkaryl or aralkyl and $R_7$ is hydrogen, $C_1$ to $C_4$ alkyl or alkenyl (including substituted alkyl or alkenyl wherein the substituents are selected from those designated as Z, above) or $C_6$ to $C_9$ aryl, alkaryl or aralkyl (including aryl, alkaryl or aralkyl having substituents selected from those defined as Z, above). Specific examples of formula (D) compounds are:
  aniline
  p-chloroaniline
  p-fluoroaniline p-nitroaniline
  p-aminobenzaldehyde
  p-aminobenzoic acid
  sodium-p-aminobenzoate
  lithium-p-aminobenzoate
  calcium di-p-aminobenzoate
  ammonium-p-aminobenzoate
  trimethylammonium-p-aminobenzoate
  tri(2-hydroxyethyl)-p-aminobenzoate
  p-aminobenzenesulfonic acid
  potassium p-aminobenzenesulfonate
  N-methylaniline
  N-propyl-N-phenylaniline
  N-methyl-N-2-propenylaniline
  N-benzylaniline
  N-(2-ethylphenyl)aniline
  4-methylaniline
  4-(2-bromoethyl)aniline
  2-(2-nitroethyl)aniline
  (4-aminophenyl)acetaldehyde
  (4-aminophenyl)acetic acid
  4-(2-propenyl)aniline
  4-(3-bromo-2-propenyl)aniline
  4-phenylaniline
  4-(3-chlorophenyl)aniline
  4-benzylaniline
  4-(4-iodobenzyl)aniline
  4-(3-ethylphenyl)aniline
  4-(2-chloro-4-ethylphenyl)aniline (E)

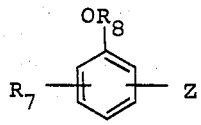

wherein Z and $R_7$ are defined as in formula (D) and $R_8$ is hydrogen or $C_1$ to $C_4$ alkyl or alkenyl (including substituted alkyl or alkenyl wherein the substituents are selected from those defined as Z in formula (D), above. Specific examples of formula (E) compounds are:
  phenol
  p-chlorophenol
  p-nitrophenol
  p-hydroxybenzaldehyde
  p-hydroxybenzoic acid
  p-hydroxybenzenesulfonic acid
  ethylphenyl ether
  2-chloroethylphenyl ether
  2-nitroethylphenyl ether
  phenoxyacetaldehyde
  phenoxyacetic acid
  3-phenoxy-1-propene
  3-phenoxy-2-nitro-1-propene
  3-phenoxy-2-bromo-1-propene
  4-propylphenol
  4-(3-bromopropyl)phenol
  2-(2-nitroethyl)phenol
  (4-hydroxyphenyl)acetaldehyde
  (4-hydroxyphenyl)acetic acid
  4-(2-propenyl)phenol
  4-phenylphenol
  4-(3-bromophenyl)phenol
  4-benzylphenol
  4-3-fluoro-2-propenyl)phenol
  4-(4-chlorobenzyl)phenol
  4-(3-chlorobenzyl)phenol
  4-(3-ethylphenyl)phenol
  4-(2-chloro-3-ethylphenyl)phenyl
  2,5-xylenol Primary oxidation dye precursors can be used alone on in combination with other primary oxidation dye precursors, and one or more primary oxidation dye precursors can be used in combination with one or more secondary oxidation dye precursors. The choice of a single oxidation dye precursor or of a particular combination of oxidation dye precursors will be determined by the color, shade and intensity of coloration which is desired. The total concentration of oxidation dye precursor in the coloring solution can be from about 0.001% to about 6% by weight and is preferably from about 0.01% to about 1.0% by weight.

Hydrogen peroxide is present in the coloring solution at a concentration of about 0.01% to about 1.0% by weight. The hydrogen peroxide which is used can be from one of the usual commercially available solutions containing 3% to 90% by weight of hydrogen peroxide. Alternatively, certain salts such as sodium perborate, which contain hydrogen peroxide in their crystal structure, can be used as sources of hydrogen peroxide. Likewise, the hydrogen peroxide can be produced by enzymatic means, e.g., by use of combination of glucose and glucose oxidase in the dyeing solution. This means of production gives a slow release of hydrogen peroxide into the dyeing solution and generally results in the requirement of a longer period of time to achieve the same dyeing effect which can be obtained by adding the required amount of hydrogen peroxide in the solution at the start of the process.

The coloring process of the present invention is preferably carried out in aqueous solution (the term solution herein, also encompasses fine dispersions or colloids of the reacting and reacted materials) but any liquid solvent medium which does not interfere with the coloring process can be used. Examples of alternative solvents are glycerol, methanol and formamide. The time of exposure of the hair to the coloring solution can be from a few seconds up to one or more hours but is preferably from about 2 to 10 minutes.

It is recognized also that conventional hair coloring products contain thickeners such as carboxymethyl cellulose, surfactants such as sodium N-laurylsarcosinate, and conditioners such as solubilized lanolin derivatives, and that such ingredients can also be utilized in the practice of the coloring process of the present invention when dyeing hair.

In a preferred manner of carrying out the process of the present invention, an aqueous mixture is prepared containing 0.1% to 1.0% by weight of hydrogen peroxide and one or more primary oxidation dye precursors and optionally one or more secondary oxidation dye precursors, the total weight percent of oxidation dye precursor in said mixture being from about 0.01% to about 1.0%. The pH of the mixture is adjusted and maintained throughout the coloring process within the range of about 5.5 to 8.0 by a suitable means such as by buffering with suitable salts (e.g., a mixture of $NaH_2PO_4$ and $Na_2HPO_4$) or by adding acid or base as needed. Soybean peroxidase is added in an amount such that the concentration of enzyme in the mixture is from about 0.05 to 100 ppm. The hair to be colored is immersed in the solution. Preferably the hair should be immersed before the addition of enzyme or as soon as practical thereafter so that as color bodies form in the solution they will become quickly affixed to the hair. After the hair has reached the desired color, (normally in about 2 to 10 minutes) it is removed from the solution, rinsed and dried.

For convenience, the soybean peroxidase enzymes and oxidation dye precursors herein can be formulated together in a composition which can be diluted to the proper usage-concentration in solution immediately prior to use. Such compositions comprise the enzyme and one or more primary, and optionally one or more secondary, oxidation dye precursors in a weight ratio of dye precursor to enzyme of from about 6,000,000:1 to 0.02:1 preferably 20,000:1 to 1:1. These compositions can be added directly to a buffered solution of hydrogen peroxide immediately before use. Although said compositions may contain only enzyme and oxidation dye precursor they normally contain these materials in combination with an inert diluent in order to facilitate handling and measuring. The diluents can be a liquid such as water so as to form a liquid concentrate or they can be solids such as inorganic salts (e.g., sodium chloride, calcium sulfate, etc.) starches, sugars, etc. Normally the total amount of enzyme and oxidation dye precursor in the compositions will be from about 0.5% to about 20% by weight, the remainder of the composition comprising the diluent materials and optionally such other materials as hair conditioners, (e.g., cationic polysiloxanes) solvents, (e.g., ethanol) surfactants, stabilizers, (e.g., sodium sulfite) thickeners (e.g., cationic cellulose derivatives) and the like.

The invention will be further illustrated by the following examples. All enzyme concentrations referred to in the examples are based on weight of pure enzyme.

EXAMPLE I

Approximately 2 grams of light brown virgin European human hair is formed into a switch by dipping one end of the hair into about 0.25 inches of glue. The hair is placed in a beaker containing 10 ml. of aqueous $NaH_2PO_4/Na_2HPO_4$ buffer (0.1 M in phosphate, pH 6) which contained 0.03% by weight hydrogen peroxide and 0.025% by weight p-phenylenediamine. (All percentages hereinafter are by weight unless specified otherwise.) 10 microliters of peroxidase stock solution containing 1 mg/ml of soybean peroxidase was added to give a final enzyme concentration of 1 ppm. The mixture was stirred for 5 minutes, then the hair was removed, rinsed in lukewarm running water and dried. After drying the hair had a medium auburn shade, compared to the original light brown shade.

When in this experiment the following secondary oxidation dye precursors are substituted on an equal weight basis for the secondary oxidation dye precursors listed in Table V, substantially similar results are obtained in that the color, shade or intensity of color produced on hair by o-phenylenediamine or p-phenylenediamine is modified: 4-methylaniline, 4-fluoroaniline, and 4-chloroaniline.

Likewise, when in this experiment the following primary oxidation dye precursors are substituted on an equal weight basis for o-phenylenediamine or p-phenylenediamine, substantially similar results are obtained in that the color, shade or intensity of color produced on hair by the primary oxidation dye precursor is modified by the secondary dye precursor; 2,4-toluenediamine, N-phenyl-p-phenylenediamine, N,N-dimethyl-p-phenylenediamine, N-methyl-p-aminophenol, o-hydroxyphenol, p-hydroxyphenol, 3,4-dihydroxybenzaldehyde, 2-methoxyphenol, 2,5-dimethoxyaniline, 3-methoxy-4-hydroxybenzaldehyde, 2-methoxy-4-(1-propenyl)-phenol, 4-methoxyphenol, p-methoxy-aniline, 4-hydroxy-3-methoxycinnamic acid, o-aminophenol, m-aminophenol, p-aminophenol, and 2-amino-1-phenol-4-sulfonic acid.

EXAMPLE II

This example illustrates the coloring of human hair with a composition of the present invention. All percentages are by weight. 60 grams of a dilute hydrogen peroxide solution buffered to pH 6 is prepared by dissolving 2 grams of an aqueous $NaH_2PO_4/Na_2HPO_4$ buffer, which is 0.1 M in phosphate. 60 grams of a dye base composition of the invention are prepared consisting of 1% p-phenylenediamine, 0.005% soybean peroxidase, 0.25% sodium sulfite (stabilizer), 5% ethanol (solvent and wetting agent), 0.2% Dow Corning EF-13574A (a cationic polysiloxane conditioner from the Dow Corning Company), 10% Varion CDG (a betaine-type surfactant from the Culver Chemical Company), 1% JR-IL (a cationic cellulose derivative thickener from Union Carbide Company) and the balance pH 6 buffer as described above. The peroxide solution and dye base composition are mixed together, and the mixture is immediately applied to the hair of a human female subject having naturally light brown hair by working it into a rich lather which remains on the hair and does not run down the neck and forehead. After working the mixture for 1 minute (to insure uniform application to all of the hair), the foamy lather is allowed to remain on the hair an additional three minutes. The subject then rinses her hair thoroughly with tap water and allows it to dry. It is observed that the hair has changed from its original light brown color to a medium auburn shade.

Hair coloring products employing oxidation hair dyes are typically marketed in kit form, i.e., a package comprising an individually packaged oxidizing component and an individually packaged oxidation dyeing component. In an embodiment of this invention, the oxidizing component consists of an aqueous solution of hydrogen peroxide having a concentration from about 0.1% to about 6% by weight, and the oxidation dyeing component comprises one or more primary oxidation dye precursors of the type hereinbefore detailed and, optionally, one or more secondary oxidation dye precursors, in a concentration of from about 0.001% to about 6% by weight and from about 0.001% to about 1% by weight of soybean peroxidase enzyme as hereinabove described. Alternatively, the enzyme can be packaged separately. The components are mixed by the user immediately prior to application to the hair. An example of such kit is as follows:

A hair dyeing kit is assembled comprising a single package including therein: (1) a 4 oz. bottle of hydrogen peroxide (1% by weight $H_2O_2$); (2) a foil packet containing an oxidation dyeing component, said component consisting of 4 g. of p-phenylenediamine, 2 g. of sodium carboxymethylcellulose (thickener), 20 g. of starch (diluent) and 0.07 g. of soybean peroxidase and 3 g. of $Na_2HPO_4/NaH_2PO_4$ (pH 7 buffer). The oxidation dyeing component is admixed with the hydrogen peroxide and the solution is applied to the hair and provides a brown-black color which is substantially shampoo-stable.

In the above kit, the p-phenylenediamine is replaced by an equivalent amount of o-phenylenediamine, 2,4-toluenediamine, N-phenyl-p-phenylenediamine, N,N-dimethyl-p-phenylenediamine, 4-nitro-o-phenylenediamine, o-hydroxyphenol, p-hydroxyphenol, 3,4-dihydroxybenzaldehyde, 2-methoxy-4-(1-propenyl)phenol, 4-methoxyphenol, p-methoxyaniline, N,N-dimethyl-p-phenylenediamine, 4-hydroxy-3-methoxycinnamic acid, o-aminophenol, m-aminophenol, p-aminophenol, 2-amino-1-phenol-4-sulfonic acid, and mixtures thereof, respectively, and shampoo-fast hair colors are secured.

What is claimed is:

1. A process for coloring hair comprising contacting hair with an effective amount of a solution containing from about 0.01 ppm to about 500 ppm of soybean peroxidase enzyme, from about 0.01% to about 1.0% by weight of hydrogen peroxide and from about 0.001% to about 6% by weight of an aromatic compound which is a primary oxidation dye precursor and having a pH of from about 4 to 10.

2. The process of claim 1 wherein the aromatic compound is selected from the group consisting of

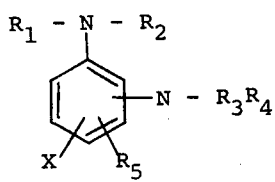

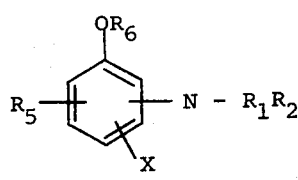

and

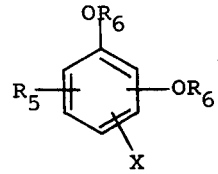

wherein X is selected from the group consisting of hydrogen, halogen, amino, hydroxyl,

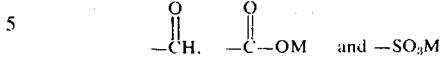

where M is hydrogen, alkali or alkaline earth metal, ammonium or substituted ammonium wherein one or more hydrogens on the ammonium ion is replaced with a 1 to 3 carbon atom alkyl or hydroxyalkyl radical, $R_1$, $R_2$, $R_3$ and $R_4$ are each selected from the group consisting of hydrogen, $C_1$ to $C_4$ alkyl and alkenyl and $C_6$ to $C_9$ aryl, alkaryl, and aralkyl, $R_5$ is selected from the group consisting of hydrogen, and alkyl and alkenyl groups having from 1 to 4 carbon atoms, and aryl, alkaryl and aralkyl groups having from 6 to 9 carbon atoms, and $R_6$ is selected from the group consisting of hydrogen, alkyl and alkenyl groups having from 1 to 4 carbon atoms, said aromatic compound being a primary oxidation dye precursor.

3. The process of claim 1 wherein the concentration of enzyme is from about 0.05 ppm to about 100 ppm.

4. The process of claim 1 wherein the primary oxidation dye precursor is selected from the group consisting of -phenylenediamine, o-phenylenediamine, 2,4-toluene-diamine, N-phenyl-p-phenylenediamine, N,N-dimethyl-p-phenylenediamine, N-methyl-p-phenylenediamine, o-hydroxyphenol, p-hydroxyphenol, 3,4-dihydroxybenzaldehyde, 2-methoxyphenol, 2,5-dimethoxyaniline, 3-methoxy-4-hydroxybenzaldehyde, 2-methoxy-4-(1-propenyl)phenol, 4-methoxyphenol, p-methoxyaniline, N,N-dimethyl-p-phenylenediamine, 4-hydroxy-3-methoxycinnamic acid, o-aminophenol, m-aminophenol, p-aminophenol, 2-amino-1-phenol-4-sulfonic acid, and mixtures thereof.

5. The process of claim 1 wherein the concentration of primary oxidation dye precursor is from about 0.01% to about 1.0% by weight.

6. The process of claim 1 wherein the pH is from about 5.5 to about 8.0.

7. A process for coloring hair comprising contacting hair with an effective amount of a solution containing from about 0.01 ppm to about 500 ppm of soybean peroxidase enzyme, from about 0.01% to about 1% by weight of hydrogen peroxide, from about 0.001% to about 6% by weight of a primary oxidation dye precursor, from about 0.01% to about 6% by weight of an aromatic compound which is a secondary oxidation dye precursor and having a pH of about 4 to 10.

8. The process of claim 7 wherein the aromatic compound is selected from the group consisting of

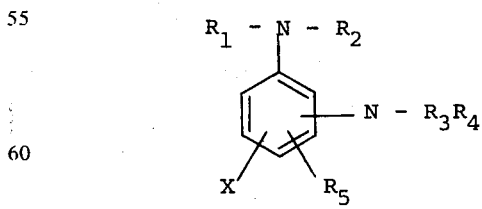

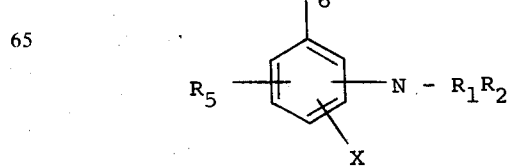

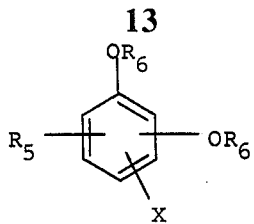

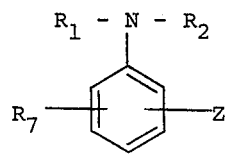

and

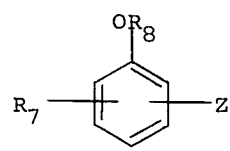

wherein X is selected from the group consisting of hydrogen, halogen, nitro, amino, hydroxyl,

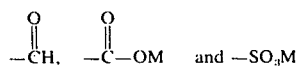

where M is hydrogen, alkali or alkaline earth metal, ammonium or substituted ammonium wherein one or more hydrogens on the ammonium ion is replaced with a 1 to 3 carbon atom alkyl or hydroxyalkyl radical, $R_1$, $R_2$, $R_3$, $R_4$, $R_5$ and $R_7$ are each selected from the group consisting of hydrogen, $C_1$ to $C_4$ alkyl and alkenyl and aryl, alkaryl, and aralkyl having 6 to 9 carbon atoms, $R_6$ and $R_8$ are each selected from the group consisting of hydrogen, alkyl and alkenyl groups having from 1 to 4 carbon atoms, Z is selected from the group consisting of hydrogen, $C_1$ to $C_3$ alkyl, halogen, nitro,

where M is hydrogen or an alkali or alkaline earth metal, ammonium or substituted ammonium wherein one or more hydrogens on the ammonium ion is replaced with a 1 to 3 carbon atom alkyl or hydroxyalkyl radical, said aromatic compound being a secondary oxidation dye precursor.

9. The process of claim 8 wherein the concentration of enzyme is from about 0.05 ppm to about 100 ppm.

10. The process of claim 8 wherein the primary oxidation dye precursor is selected from the group consisting of p-phenylenediamine, o-phenylenediamine, 2,4-toluenediamine, N-phenyl-p-phenylenediamine, N,N-dimethyl-p-phenylenediamine, N-methyl-p-phenylenediamine, N-methyl-p-phenylenediamine, o-hydroxyphenol, p-hydroxyphenol, 3,4-dihydroxybenzaldehyde, 2-methoxyphenol, 2,5-dimethoxyaniline, 3-methoxy-4-hydroxybenzaldehyde, 2-methoxy-4-(1-propenyl)phenol, 4-methoxyphenol, p-methoxyaniline, N,N-dimethyl-p-phenylenediamine, 4-hydroxy-3-methoxycinnamic acid, o-aminophenol, m-aminohenol, p-aminophenol, 2-amino-1-phenol-4-sulfonic acid, and mixtures thereof, and the secondary oxidation dye precursor is selected from the group consisting of aniline, p-toluidine, p-fluoroaniline, p-chloroaniline, p-hydroxybenzaldehyde, 2,4-dihycorxybenazldehyde, 2,5-xylenol, and mixtures thereof.

11. The process of claim 8 wherein the total concentration of primary and secondary oxidation dye precursors is from about 0.01% to about 1% by wieght.

12. The process of claim 8 wherein the pH is from about 5.5 to about 8.0.

13. A composition of matter comprising a primary oxidation dye precursor and a peroxidase soybean enzyme at a weight ratio of primary oxidation dye precursor to enzyme of from about 6,000,000:1 to about 0:2:1.

14. The composition of claim 13 wherein the oxidation dye precursor is selected from the group consisting of p-phenylenediamine, o-phenylenediamine, 2,4-toluenediamine, N-phenyl-p-phenylenediamine, N,N-dimethyl-p-phenylenediamine, N-methyl-p-phenylenediamine, o-hydroxyphenol, p-hydroxyphenol, 3,4-dihyroxybenzaldehyde, 2-methoxy-4-(1-propenyl)-phenol, 4-methoxyphenol, p-methoxyaniline, N,N-dimethyl-p-phenylenediamine, 4-hydroxy-3-methoxycinnamic acid, o-amino-phenol, m-aminophenol, 2-amino-1-phenol-4-sulfonic acid and mixtures thereof.

15. A process for coloring hair comprising contacting hair with an effective amount of a solution containing from about 0.01% to about 1.0% by weight of hydrogen peroxide and from about 0.001% to about 6% by weight of an aromatic compound which is a primary oxidation dye precursor wherein the solution has a pH of from about 4 to 10 and thereafter contacting the hair with an effective amount of a solution containing from about 0.01 ppm to about 500 ppm of soybean peroxidase enzyme, from about 0.01% to about 1.0% by weight of hydrogen peroxide and from about 0.001% to about 6% by weight of an aromatic compound which is a primary oxidation dye precursor wherein the solution has a pH of from about 4 to 10.

* * * * *

UNITED STATES PATENT OFFICE
CERTIFICATE OF CORRECTION

PATENT NO. : 3,957,424
DATED : May 18, 1976
INVENTOR(S) : Eugene Zeffren and John Francis Sullivan It is certified that error appears in the above-identified patent and that said Letters Patent are hereby corrected as shown below:

Column 2, line 6, "peroxides" should read -- peroxidase --;
column 2, line 51 "aligomers" should read -- oligomers --.
Column 7, line 8, "earch" should read -- earth --; column 7, line 24, "p-fluoroaniline p-nitroaniline" should read
        -- p-fluoroaniline
           p-nitroaniline --.
Column 8, line 26, "4-(2-chloro-3-ethylphenyl)phenyl" should read -- 4-(2-chloro-3-ethylphenyl)phenol --; column 8, line 29, "on" should read -- or --.

Claim 10, column 14, line 13, "henol" should read -- phenol --;
Claim 13, column 14, line 25, "peroxidase soybean" should read -- soybean peroxidase --.
Claim 14, column 14, line 39, after "m-aminophenol" insert -- p-aminophenol --.

Signed and Sealed this

Twenty-fourth Day of August 1976

[SEAL]

Attest:

RUTH C. MASON
Attesting Officer

C. MARSHALL DANN
Commissioner of Patents and Trademarks